United States Patent
Ochi et al.

(10) Patent No.: US 10,105,040 B2
(45) Date of Patent: Oct. 23, 2018

(54) IMAGING NEEDLE APPARATUS

(71) Applicant: Samark Technology LLC, Sarasota, FL (US)

(72) Inventors: Sam Seiichiro Ochi, Lakewood Ranch, FL (US); Mark Walter, Sarasota, FL (US)

(73) Assignee: NANOSURGERY TECHNOLOGY CORPORATION, Sarasota, FL (US)

( * ) Notice: Subject to any disclaimer, the term of this patent is extended or adjusted under 35 U.S.C. 154(b) by 230 days.

(21) Appl. No.: 15/036,609

(22) PCT Filed: May 6, 2016

(86) PCT No.: PCT/US2016/031319
§ 371 (c)(1),
(2) Date: May 13, 2016

(87) PCT Pub. No.: WO2016/182946
PCT Pub. Date: Nov. 17, 2016

(65) Prior Publication Data
US 2017/0100020 A1    Apr. 13, 2017

Related U.S. Application Data

(60) Provisional application No. 62/159,182, filed on May 8, 2015.

(51) Int. Cl.
*A61B 1/05* (2006.01)
*A61B 1/06* (2006.01)
(Continued)

(52) U.S. Cl.
CPC .......... *A61B 1/042* (2013.01); *A61B 1/00016* (2013.01); *A61B 1/00018* (2013.01);
(Continued)

(58) Field of Classification Search
CPC ... A61B 1/05; A61B 1/00016; A61B 1/00018; A61B 1/0008; A61B 1/0615; A61B 1/0684; A61B 1/015; A61B 1/051; A61B 1/317; A61B 17/34; A61B 17/3437; A61B 17/3478; A61B 2010/045; A61B 10/0283; A61B 2018/1869; A61M 5/32
See application file for complete search history.

(56) References Cited

U.S. PATENT DOCUMENTS 5,083,101 A * 1/1992 Frederick ............. H03H 1/0007
                                                        333/12
5,345,592 A * 9/1994 Woodmas ............... H04H 60/05
                                                        340/12.32
(Continued)

FOREIGN PATENT DOCUMENTS

| EP | 2 494 914 A1 | 9/2012 | |
| JP | 2011078682 A * | 4/2011 | ......... A61B 1/00165 |
| WO | WO 2012/028840 A1 | 3/2012 | |

OTHER PUBLICATIONS

International Search Report and Written Opinion for PCT/US2016/031319, dated May 6, 2016.

*Primary Examiner* — John P Leubecker (57) ABSTRACT

An imaging device includes a needle, an imager, and a syringe. The needle includes a tip. The imager includes a plurality of stacked integrated circuits (ICs). The syringe is coupled to the needle.

14 Claims, 7 Drawing Sheets

(51) Int. Cl.
*A61B 1/317* (2006.01)
*A61B 1/04* (2006.01)
*A61B 1/00* (2006.01)
*A61B 1/015* (2006.01)
*A61B 17/34* (2006.01)

(52) U.S. Cl.
CPC .......... *A61B 1/00045* (2013.01); *A61B 1/015* (2013.01); *A61B 1/051* (2013.01); *A61B 1/0615* (2013.01); *A61B 1/0684* (2013.01); *A61B 1/317* (2013.01); *A61B 1/05* (2013.01); *A61B 17/3478* (2013.01)

(56) References Cited

U.S. PATENT DOCUMENTS

| | | | | |
|---|---|---|---|---|
| 5,385,572 | A * | 1/1995 | Nobles | A61B 1/042 604/264 |
| 5,940,126 | A * | 8/1999 | Kimura | H04N 3/1593 348/218.1 |
| 6,352,503 | B1 * | 3/2002 | Matsui | A61B 1/00071 600/104 |
| 6,387,043 | B1 * | 5/2002 | Yoon | A61B 1/00052 600/104 |
| 6,659,941 | B2 * | 12/2003 | Weber | A61B 1/00082 600/104 |
| 7,436,494 | B1 * | 10/2008 | Kennedy | G01S 7/487 356/4.01 |
| 7,927,272 | B2 * | 4/2011 | Bayer | A61B 1/00154 600/107 |
| 8,834,358 | B2 * | 9/2014 | Mckinley | A61B 17/3421 600/117 |
| 9,013,615 | B2 * | 4/2015 | Kirsch | H04N 5/341 348/222.1 |
| 9,631,781 | B2 * | 4/2017 | Ide | F21K 9/64 |
| 9,851,411 | B2 * | 12/2017 | Champlin | G01R 31/3624 |
| 2002/0175992 | A1 * | 11/2002 | Eino | A61B 1/00048 348/65 |
| 2005/0173807 | A1 * | 8/2005 | Zhu | H01L 25/0652 257/777 |
| 2006/0173284 | A1 * | 8/2006 | Ackerman | G01R 33/287 600/422 |
| 2006/0224040 | A1 * | 10/2006 | Khait | A61B 1/041 600/102 |
| 2008/0183080 | A1 * | 7/2008 | Abraham | A61B 1/3132 600/466 |
| 2008/0188767 | A1 * | 8/2008 | Oaki | A61B 1/018 600/566 |
| 2008/0195128 | A1 * | 8/2008 | Orbay | A61B 1/00048 606/170 |
| 2010/0145146 | A1 * | 6/2010 | Melder | A61B 1/00052 600/112 |
| 2010/0165087 | A1 * | 7/2010 | Corso | G06K 9/32 348/65 |
| 2010/0198009 | A1 | 8/2010 | Farr et al. | |
| 2010/0274081 | A1 * | 10/2010 | Okoniewski | A61B 17/3474 600/109 |
| 2011/0245605 | A1 | 10/2011 | Jacobsen et al. | |
| 2011/0261183 | A1 * | 10/2011 | Ma | A61B 90/361 348/77 |
| 2012/0101330 | A1 * | 4/2012 | Goldenberg | A61B 1/015 600/109 |
| 2013/0023769 | A1 | 1/2013 | Tsai et al. | |
| 2014/0066711 | A1 * | 3/2014 | Farin | A61B 1/0684 600/109 |
| 2014/0364691 | A1 * | 12/2014 | Krivopisk | A61B 1/00096 600/109 |
| 2015/0031946 | A1 * | 1/2015 | Saadat | A61B 1/05 600/104 |
| 2015/0173592 | A1 * | 6/2015 | Leeflang | A61B 17/3478 600/106 |
| 2015/0313634 | A1 * | 11/2015 | Gross | A61B 1/0676 606/185 |
| 2015/0327754 | A1 * | 11/2015 | Leeflang | A61B 1/05 600/104 |
| 2015/0342621 | A1 * | 12/2015 | Jackson, III | A61B 5/6878 600/546 |
| 2016/0022117 | A1 * | 1/2016 | Akahane | G02B 23/2476 348/65 |
| 2016/0081712 | A1 * | 3/2016 | Heniford | A61B 5/0066 600/424 |
| 2017/0042573 | A1 * | 2/2017 | Savvouras | A61B 17/3474 |
| 2017/0086666 | A1 * | 3/2017 | Kienzle | A61B 1/0684 |
| 2017/0252537 | A1 * | 9/2017 | Hayashi | A61M 25/0084 |
| 2017/0319317 | A1 * | 11/2017 | Biscay | A61D 19/027 |

\* cited by examiner

IMAGING NEEDLE APPARATUS

CROSS-REFERENCE TO RELATED APPLICATION

The present application is a National Stage of International Patent Application No. PCT/US16/31319 filed on May 6, 2016, which claims the benefit of U.S. Provisional Application No. 62/159,182, filed on May 8, 2015, which are incorporated by reference.

BACKGROUND

Traditional surgical procedures are open procedures. In an open surgical procedure, a surgeon makes a large incision on a patient in order to view and correct physical ailments using surgical tools. Open procedures have several drawbacks. The large surgical incisions used to perform open procedures can become infected. Surgeons may damage surrounding tissues during open procedures, while trying to manipulate the surgical site. Open procedures often require patients to undergo full anesthesia, which independently increases risks of death and/or serious complications. In addition, open procedures can cause patients severe discomfort during recovery periods.

In order to avoid the complications of open procedures, surgeons have developed minimally invasive surgical techniques to perform surgeries that were traditionally performed as open procedures. In contrast to open procedures, minimally invasive procedures can be performed by inserting surgical tools through small incisions in a patient's skin. Minimally invasive procedures have various advantages over open procedures, including lower infection risks, lower patient discomfort, and lower anesthesia requirements.

The small incisions used in minimally invasive procedures make viewing the surgical field difficult. Accordingly, surgeons generally use imaging devices, e.g., endoscopes, during minimally invasive procedures in order to indirectly view the surgical field. Some of these imaging devices must be inserted into a patient's body through the small incisions.

Arthroscopy is a type of minimally invasive orthopedic procedure performed in a skeletal joint cavity. An arthroscope includes a camera that may be inserted directly into a skeletal joint. With help from the arthroscope, surgeons can diagnose various problems related to the skeletal joint.

In certain cases, arthroscopes can be used to determine whether a therapeutic material should be delivered to the skeletal joint. For example, a surgeon may use an arthroscope to determine whether to deliver a drug, stem cells, or anesthesia for a future procedure to the skeletal joint. Some of these therapeutic materials can be injected using a syringe and a needle.

SUMMARY

The present disclosure relates to an imaging needle apparatus. Various exemplary imaging needle apparatuses are described below.

An imaging device may include a needle including a tip, an imager disposed on the needle, and a syringe coupled to the needle. The imager may include a plurality of stacked integrated circuits (ICs).

The imager may include an imaging chip stacked on the plurality of stacked ICs, and the may further include a light-emitting diode (LED) provided proximate the imager, and a bypass capacitor disposed inside of the needle and proximate the imager.

The imaging chip may include an array of pixels.

The plurality of stacked ICs may include a first plurality of complementary metal-oxide semiconductor (CMOS) chips having a first size, and a second plurality of CMOS chips having a second size that is larger than the first size. The first plurality of CMOS chips may be disposed between the imaging chip and the plurality of second CMOS chips.

The imager may be provided on a side of the needle.

The imager may be provided proximate on a front of the needle.

The one or more wires may be a single coaxial wire comprising an inner conductor that transmits data from the imager, an outer conductor connected to ground, a dielectric layer disposed between the inner conductor and the outer conductor, and an outer insulating jacket covering the outer conductor.

The one or more wires may be a single coaxial wire comprising an inner conductor that transmits data from the imager, a middle conductor connected to ground, a first dielectric layer disposed between the inner conductor and the middle conductor, an outer conductor connected to a power terminal, and a dielectric layer disposed between the middle conductor and the outer conductor.

An imaging system may include an imaging device including a needle having a tip, an imager disposed on the needle, a syringe coupled to the needle, and a display electrically coupled to the imaging device. The imager may include a plurality of stacked integrated circuits (ICs) and an imaging chip stacked on the plurality of stacked ICs.

The imaging device may be electrically coupled to the display via a universal serial bus (USB) wire.

The imaging device may be wirelessly coupled to the display.

The imaging chip may include an array of pixels.

The plurality of stacked ICs may include a first plurality of complementary metal-oxide semiconductor (CMOS) chips having a first size, and a second plurality of CMOS chips having a second size that is larger than the first size. The first plurality of CMOS chips may be disposed between the imaging chip and the plurality of second CMOS chips.

The imaging system may further include a wire output disposed on the syringe, and one or more wires coupled between the imager and the wire output. The one or more wires may be disposed inside of the needle.

The one or more wires may be a single coaxial wire including an inner conductor that transmits data from the imager, an outer conductor connected to ground, a dielectric layer disposed between the inner conductor and the outer conductor, and an outer insulating jacket covering the outer conductor.

The one or more wires may be a single coaxial wire including an inner conductor that transmits data from the imager, a middle conductor connected to ground, a first dielectric layer disposed between the inner conductor and the middle conductor, an outer conductor connected to a power terminal, and a dielectric layer disposed between the middle conductor and the outer conductor.

DETAILED DESCRIPTION OF THE EMBODIMENTS

The present disclosure relates to an imaging needle apparatus. The apparatus can take pictures, or video, or both using an image capturing device or imager. The image capturing device or imager may be proximately located to a needle. In an embodiment, the apparatus is a video syringe and is capable of capturing images and injecting fluid into a desired location, e.g., at a knee or shoulder joint of a person. In an embodiment, the fluid may be stem cell fluid, drugs, or other fluid used for medical treatment.

Figure 1:
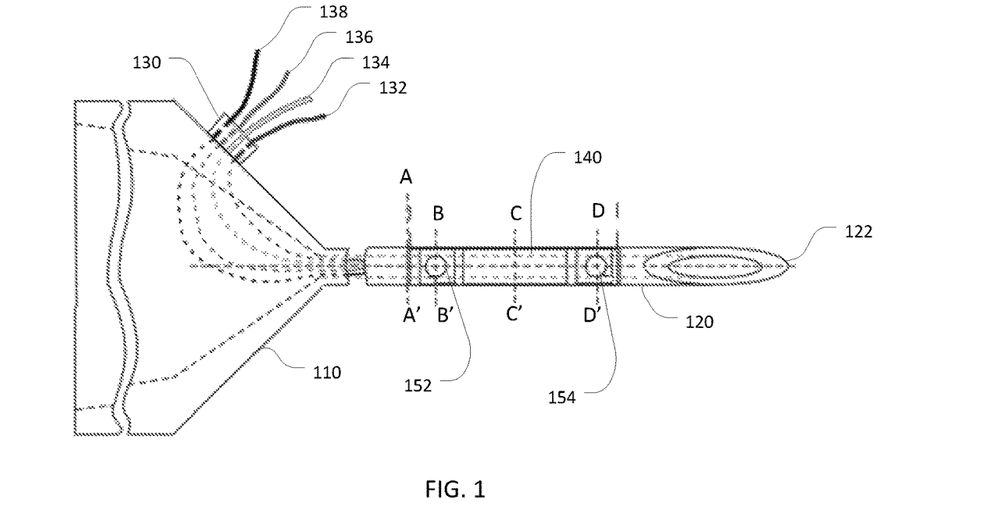
FIG. 1 illustrates an imaging apparatus according to an embodiment of the present disclosure.
Figure 2:
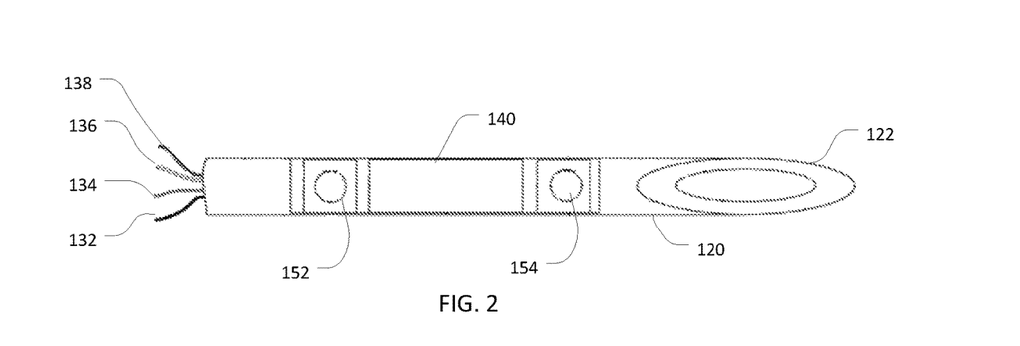
FIG. 2 illustrates a needle the imaging apparatus from a first side view according to an embodiment of the present disclosure.
Figure 3:
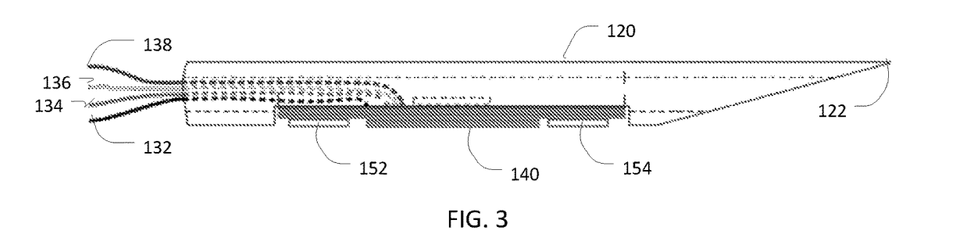
FIG. 3 illustrates the needle of the imaging apparatus from the second view according to an embodiment of the present disclosure.

FIG. 1 shows an imaging apparatus 100 according to an embodiment of the present disclosure. The imaging apparatus 100 may include a syringe 110, a needle 120, a wire output 130, an imager 140, and first and second light-emitting diodes (LEDs) 152 and 154. FIGS. 2 and 3 illustrate the needle 120 from first and second side views according to an embodiment of the present disclosure.

The syringe 110 may be used to inject fluid through the needle 120. The syringe 110 may be hollow, and may stably house fluid before the fluid is injected through the needle 120. The syringe 110 may exert a positive pressure on the fluid in order to propel the fluid through the needle 120. The syringe 110 may push fluid in a direction that is parallel to the needle 120, such that the fluid can be propelled through the needle 120 with relatively laminar flow. That is, the position of the syringe 110 with respect to the needle 120 prevents fluids from turbulently flowing through the needle 120.

The syringe 110 may include a plunger or a pump that may propel the fluid through the needle 120. When the syringe 110 includes a plunger, a user can deliver fluid through the needle 120 by pushing the plunger toward the needle 120 in a direction parallel to the needle 120.

The needle 120 may include a sharp tip 122 that can pierce soft tissue. Although not illustrated, the sharp tip 122 may be configured to be retractable into the needle 120 so that the needle 120 would have a blunt tip (not shown) when the sharp tip 122 is retracted into the needle 120. In an embodiment, the needle 120 can pierce soft tissue around a skeletal joint, such as a knee.

As shown by FIG. 3, the tip 122 of the needle 120 may be tapered. The needle 120 may be a hypodermic needle. The tip 122 may be comprised of stainless steel. In an embodiment, an outer diameter of the needle may be between 0.0280 inches and 0.0285 inches, and an inner diameter of the needle may be between 0.0155 and 0.0175 inches. The needle 120 may be a 22-gauge hypodermic needle. In an embodiment, the needle 120 includes a flat outer surface attached to the imager 140. The imager 140 may be placed in other locations, e.g., on the front of the needle 120.

A fluid path may be provided within the needle 120 for fluid that may be injected into a specific site. The fluid may include, e.g., a fluid drug or stem cell fluid. When the syringe 110 increases pressure in the fluid path, the fluid can be emitted from the tip 122 of the needle 120.

In an embodiment, the needle 120 includes a first path for the wires and a second, separate path for injecting fluid. In another embodiment, the needle 120 has a single path shared by output wires from the imager 140 and the fluid.

The needle 120 may be attached or detached from the syringe 110. In an embodiment, the bayonet of the needle 120 may screw onto threads disposed on an attachment point of the syringe 110.

The wire output 130 may be coupled to one or more conductive wires that output imaging data from the imager 140. The wire output 130 may be further coupled to one or more wires that supply power to the imager 140. In other embodiments, however, fewer or additional wires may be coupled to the wire output 130.

The wire output 130 may be coupled to a battery, and may transfer power from the battery to the imager. In an embodiment, the wire output 130 transfers power to the imager from an external device, such as an external display device, via a wired or wireless connection.

The wire output 130 may include one or more processors that convert the imaging data from the imager 140 to a standard video format. In an embodiment, the wire output 130 receives imaging data from the imager 140. The imaging data may be in the standard video format, e.g., Universal Serial Bus (USB) or High-Definition Multimedia Interface (HDMI) compatible.

The wire output 130 may convert one or more of the wires transferring imaging data and/or power to and from the imager 140 into a single output wire. In an embodiment, the wire output 130 may output the one or more signal and power wires to a single socket or plug that may interface with an external display device. The socket or plug may be a USB or an HDMI socket or plug, or other communication interfaces. The external display device may thus display imaging data from the imager 140 and may power the imager 140 via the wire output 130.

In an embodiment, the imaging needle apparatus includes or is coupled to a communication component (not shown) that wirelessly transmits the imaging data to an external display device 1220 (see FIG. 12) using Bluetooth or Wi-Fi, or other wireless communication protocols.

Referring back to FIG. 1, four wires are coupled between the wire output 130 and the imager 140. The wires may include a positive power wire 132, a negative power wire 134, a positive data wire 136, and a negative data wire 138.

Each of the wires 132, 134, 136, and 138 may include a conductive material and an insulative material that covers the conductive material. In an embodiment, each wire has a diameter of about 75 µm. The wires may be color coded: for example, the positive power wire 132 may be red, the positive data wire 136 may be white, the negative data wire 138 may be green, and the negative power wire 134 may be black.

One or more of the wires 132, 134, 136, and 138 may be micro-coaxial wires, as discussed below with respect to FIGS. 8 through 11. In an embodiment, all of the wires 132, 134, 136, and 138 are integrated into a single micro-coaxial wire with a data bypass capacitor and a power supply bypass capacitor.

The wires 132, 134, 136, and 138 may protrude from the imager 140 into the interior of the needle 120. The wires 132, 134, 136, and 138 may be threaded within the interior of the needle 120, pass through a bayonet of the needle 120, and disposed in an interior space of the syringe 110, and attach to an interior side of the wire output 130. The wires 132, 134, 136, and 138 may be electrically coupled between the imager 140 and the wire output 130.

The imager 140 may be used to capture images and/or video of spaces and structures disposed in the vicinity of the needle 120. The imager 140 may capture images and/or video in one or more directions with respect to the needle 120. The imager 140 may, for example, capture images and/or video in a radial direction with respect to the needle 120. The imager 140 may output the images and/or video as imaging data.

The imager 140 may be fixed at a position proximate to the needle 120. For example, the imager 140 may be attached to an outer surface of the needle 120. The imager 140 may be attached to the outer surface of the needle 120 with an adhesive. In an embodiment, the imager 140 is fixed on an outside surface of the needle 120 at a position within ⅛ to ½ inches of the tip 122. In an embodiment, the imager 140 may be attached to a flat exterior surface of the needle 120.

In an embodiment, the imager 140 includes a complementary metal-oxide semiconductor (CMOS) imager. The imager 140 may include a plurality of image sensors corresponding to a plurality of pixels. The image sensors may be a plurality of imaging chips disposed along a flat surface, for example.

The imager 140 may include one or more controllers coupled between the communication interface and the circuits in the rest of the imager 140. The imager 140 may further include analog and digital control electronics that convert imaging signals from the imager 140 to signals compatible with a communication interface. The imager 140 may include electronics that converts raw imaging data to imaging data that is compatible with the wire output 130 and/or external display device. For example, the imager 140 may convert the raw imaging data to uncompressed video imaging data compatible with a USB- or HDMI-based interface.

The imager 140 may output data to a first bypass capacitor that is coupled between the imager 140 and the positive and negative data wires 136 and 138. In addition, a second bypass capacitor may be coupled between the imager 140 and the positive and negative data wires 132 and 134. The first and second bypass capacitors may reduce noise in signals transmitted through the wires 132, 134, 136, and 138.

The first and second LEDs 152 and 154 may illuminate areas around the needle 120, in order to more easily capture high quality images using the imager 140. In an embodiment, one or both of the first and second LEDs 152 and 154 emits white light. The first and second LEDs 152 and 154 may be integrated into the imager 140. In an embodiment, the first and second LEDs 152 and 154 each emit light from a surface having an area of 680 µm by 680 µm.

In an embodiment, the first LED 152 may be located between the imager 140 and the syringe 130. The second LED may be located between the imager 140 and the tip 122 of the needle 120.

Although two LEDs are illustrated, embodiments are not so limited. The apparatus 100 may include more or fewer than two LEDs.

The imager 140 and the first and second LEDs 152 and 154 may be covered with a clear, biocompatible sealant (not shown). The sealant may fix the imager 140 and the first and second LEDs 152 and 154 onto the needle 120, such that components of the imager 140 and the first and second LEDs 152 and 152 do not become dislodged. e.g., by human tissue, when the imaging apparatus 100 is used during a medical procedure. In addition, the sealant may cover the imager 140 and the first and second LEDs 152 and 154 with a smooth surface, such that the needle 120 can be smoothly inserted into a desired site.

FIGS. 4 through 7 show cross sections of the needle 140 according to an embodiment of the present disclosure.

Figure 4:
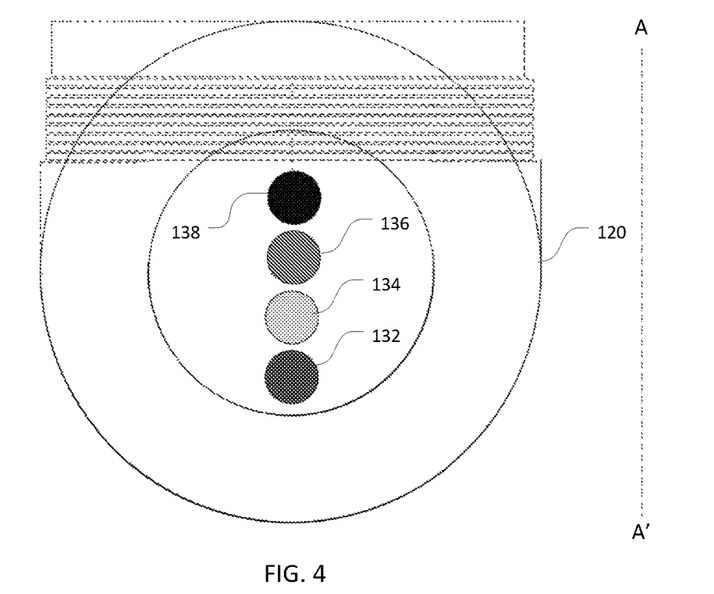
FIG. 4 illustrates a cross-section of the needle of the imaging apparatus along a line A-A' according to an embodiment of the present disclosure.

FIG. 4 illustrates a cross section of the needle 120 between the syringe 130 and the imager 140 along a line A-A' illustrated in FIG. 1. FIG. 4 shows that the outer surface of the needle 120 may be rounded where the imager 140 is not present.

Figure 5:
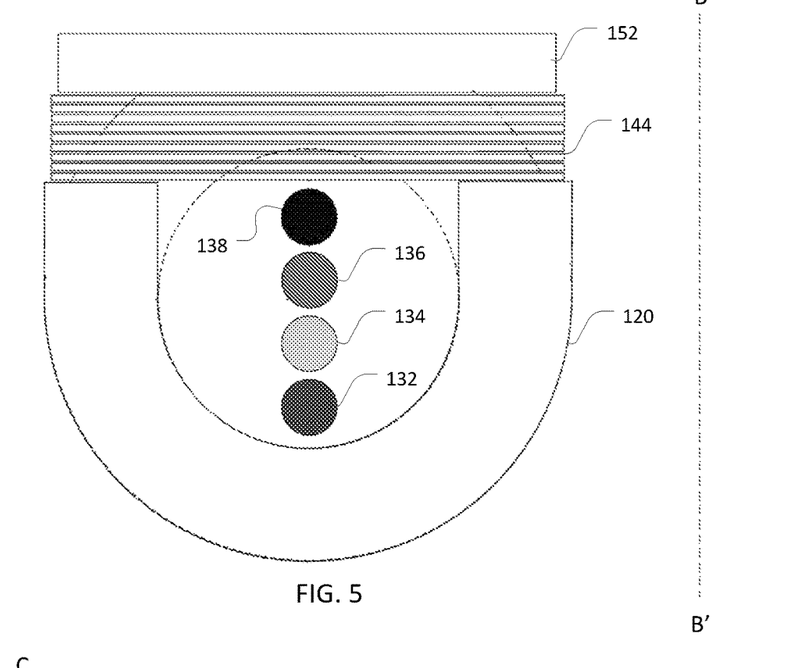
FIG. 5 illustrates a cross-section of the needle of the imaging apparatus along a line B-B' according to an embodiment of the present disclosure.

FIG. 5 shows a cross section of the needle 120, the first LED 152, the imager 140, and the wires 132, 134, 136, and 138 along a line B-B' illustrated in FIG. 1.

The first LED 152 may be disposed on the imager 140. The first LED 152 may emit light in a direction that points away from the needle 120 and in an imaging direction of the imager 140.

The imager 140 may be disposed between the first LED and the needle 120. The imager 140 may include a plurality of stacked chips. The stacked chips of the imager 140 may include an imaging chip 142 and an integrated circuit (IC) stack 144. The IC stack 144 may include, for example, silicon CMOS circuits. Each stacked chip may have a thickness of approximately 10 µm or less. In an embodiment, one or more stacked chips are each 5-8 µm thick. The imaging chip 142 may be located on top of the stack of control ICs 144. The number of ICs in IC stack 144 may vary depending on the implementation.

The first and second LEDs 152 and 154 as well as the first stack, may be located above the second stack of the imager 140. That is, the first and second LEDs 152 and 154 may be stacked on the imaging chip 142.

In an embodiment, the first LED 152 and the imager 140 are flat structures and may be attached to an outer surface of the needle 120. Accordingly, the device 100 may have a flat side where the imager 140 is attached to the outer surface of the needle 120, even though rest of the outer surface of the needle 120 may be curved.

In an embodiment, the outer corners of the imager 140 may be rounded, such that the needle 120 and the imager 140 together provide a round, elongated shape resembling a conventional, cylindrical needle. In an embodiment, one or more of control ICs in the imager 140 may fixed to an interior surface of the needle 120, such that the imager 140 may be partially disposed inside of the needle 120.

The wires 132, 134, 136, and 138 may extend from the imager 140 into the interior of the needle 120 and underneath the imager 140 and the first LED 152.

As shown in FIGS. 4 and 5, the wires 132, 134, 136, and 138 may have small cross-sectional areas compared to the interior of the needle, which may provide ample interior space for fluids to be injected from the tip 122 of the needle 120 with substantially laminar flow. In an embodiment, the cross-sectional area of the wires 132, 134, 136, and 138 may take up between 5 and 25% of the interior cross-sectional area of the needle 120.

In an embodiment, the wires 132, 134, 136, and 138 may be fixed to an interior surface of the needle 120, in order to provide a more continuous fluid path through the needle 120. The wires 132, 134, 136, and 138 may be glued to the interior surface of the needle 120.

Figure 6:
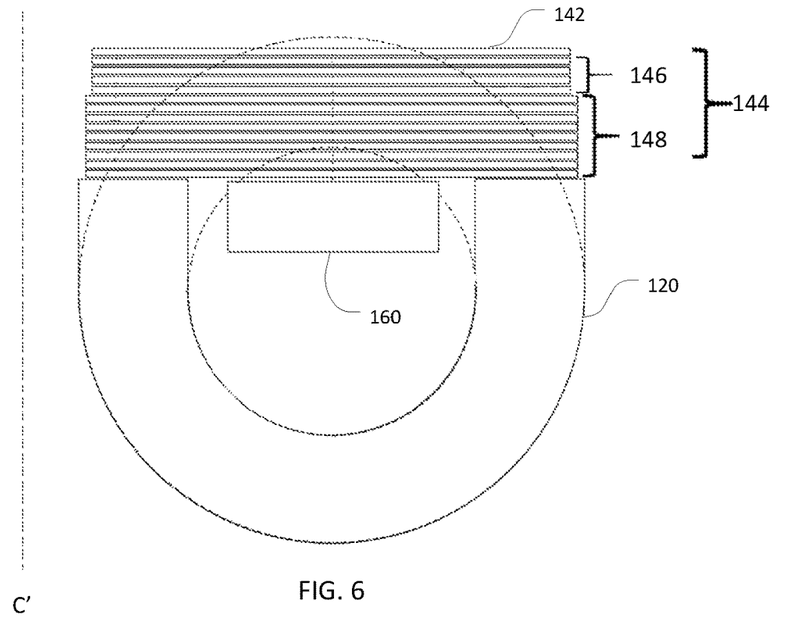
FIG. 6 illustrates a cross-section of the needle of the imaging apparatus along a line C-C' according to an embodiment of the present disclosure.

FIG. 6 illustrates a cross-section of the needle 120, the imager 140, and a bypass capacitor 160 along a line C-C' according to an embodiment of the present disclosure. Specifically, FIG. 6 shows a cross-section of the imaging chip 142 and the IC stack 144 of the imager 140.

The imaging chip 142 may be disposed on top of the IC stack 144. The imaging chip 142 may include a plurality of imaging sensors corresponding to pixels. In an embodiment, the imaging chip 142 is a 1.36 mega pixel imager, and may include a 1 $\mu m^2$ pixel array located over an area of 680 $\mu m$ by 2000 $\mu m$ on top of the IC stack 144.

The imaging chip 142 may convert image signals into electrical signals, and may pass the electrical signals to circuitry in the IC stack 144.

The IC stack 144 may include a plurality of ICs. In an embodiment, the plurality of ICs in the IC stack 144 may be divided into a first plurality of ICs in a first stack 146 and a second plurality of ICs in a second stack 148. Each of the plurality of ICs in the IC stack 144 may include a silicon wafer.

The first stack 146 may be stacked on top of the second stack 148, between the imaging chip 142 and the second stack 148. In an embodiment, the first stack 146 may include a stack of four CMOS ICs. In an embodiment, each of the CMOS ICs has a stacking surface with an area of a first size, for example, 680 $\mu m$ by 2000 $\mu m$.

The second stack 148 may be disposed between the bypass capacitor 160 and the first stack 146. In an embodiment, the second stack 148 includes a first logic layer, a plurality of bit layers, and a second logic layer. The first logic layer (the "controller") may contain sense amps, write drivers, address decoders, and other elements that read and write memory bits. The plurality of bit layers may be stacked on the first logic layer. The second logic layer (the "I/O layer") may be attached underneath the controller and the plurality of bit layers. The I/O layer translates a signal from the controller according to a voltage and protocol that is understandable by an off-chip device, such as a processor, a field-programmable gate array (FPGA), an optical link, or other device.

In an embodiment, the second stack 148 may include 9 CMOS ICs. In an embodiment, each of the CMOS ICs has a stacking surface with an area of a second size that is larger than the first size, for example, 710 $\mu m$ by 4000 $\mu m$. Alternatively, the second stack 148 may include 9 CMOS ICs that may each have a surface with an area of 700 $\mu m$ by 4000 $\mu m$.

The second stack 148 may therefore have a larger width than the first stack 146 and the imaging chip 142. In addition, the second stack 148 may have a larger length than the first stack 146 or the imaging chip 142. Accordingly, the outer surface of the imager 140 may have slightly rounded edges, so that the needle 120 may be smoothly inserted into a desired surgical site.

In an embodiment, the first stack 146 and the imaging chip 142 may have substantially the same height as each of the first and second LEDs 152 and 154. A surgical-grade material may be disposed between the first stack 146 and the imaging chip 142 and the first and second LEDs 152 and 154, so that the apparatus 100 has a smooth outer surface.

The plurality of ICs in the IC stack 144 may be interconnected by through silicon vias (TSVs) and contacts. In some embodiments, the IC stack 144 and the imaging chip 142 may include copper TSVs and contacts. Alternatively or additionally, the IC stack 144 and the imaging chip 142 may include tungsten TSVs and contacts.

Tungsten TSVs and contacts provide a number of advantages over copper TSVs and contacts. Advantages of ICs with tungsten include better thermal compatibility, size, and density than ICs with copper alone.

Tungsten is more thermally compatible with silicon than copper. Tungsten and silicon have similar coefficients of thermal expansion. Accordingly, tungsten TSVs and contacts apply limited physical distress on surrounding a silicon wafer during operating conditions.

In addition, tungsten structures may be smaller than copper structures, and may therefore may have almost negligible inductance, capacitance, and resistance. Accordingly, tungsten contacts may be more cheap and reliable than copper contacts. For example, the tungsten contacts in the IC stack 144 may fill a 10 $\mu m$ deep hole with a 10:1 aspect ratio. In an embodiment, the tungsten TSVs can have diameters of 1 $\mu m$ or less, even with a 10:1 aspect ratio limit, when a wafer thickness is 10 $\mu m$ or less. In an embodiment, the tungsten contacts may also be 1 $\mu m$ (or less) wide, and arrayed on a 2 $\mu m$ or smaller pitch (the center to center distance between repeated objects). Thus, embodiment of the IC stack 144 may include tungsten TSVs and contacts instead of larger copper through silicon vias (TSVs).

In contrast, copper TSVs may have a larger width than tungsten TSVs. For example, the copper TSVs in the IC stack 144 may be 5 $\mu m$ wide and located on a 40 to 50 $\mu m$ pitch. Copper is less thermally compatible with silicon than tungsten. That is, copper has a different thermal coefficient of expansion than silicon.

Tungsten can also be used to fabricate a more densely connected IC than copper alone. In an embodiment, a wafer in the IC stack 144 includes 5 $\mu m$ wide copper TSVs spaced on a grid of 40 or more $\mu m$ per step, and may alternatively or additionally include tungsten contacts can be organized on a pitch that is about two times the contact diameter, (e.g. 0.6 $\mu m$ wide contacts can be on a 1.2 $\mu m$ pitch, and 1 $\mu m$ wide contacts can be on a 2 $\mu m$ pitch). Thus, the tungsten contacts in the IC stack 144 may be made with very small diameters, and can also be arrayed on a very tight pitch. Thus, tungsten TSVs and contacts support a higher vertical interconnect per unit area across the surface of each wafer in the IC stack 144 than copper TSVs and contacts, and therefore support higher interconnect.

In an embodiment, the wafers of the IC stack 144 include only tungsten TSVs or contacts, or only a limited number of copper TSVs and contacts. In an embodiment, when a wafer of the IC stack 144 includes too much copper, a normal temperature change can break the wafer. Even if the die or wafer does not break, if a transistor is located too close to the copper TSV, the expansion or contraction of the copper can change the operating characteristics of the transistor, and may make the rest of the IC non-functional.

Due to high vertical interconnect from tungsten and copper TSVs and contacts, it is possible to perform potent and comprehensive post-assembly repair of the ICs in the IC stack 144. In an embodiment, a variety of redundant circuit elements are available, including spare contacts. In addition, redundant elements from one die may be used to repair defects in another die in the IC stack 144. The IC stack 144 may become more reparable by adding more dies to the stack.

That is, because the IC stack 144 may include small tungsten TSVs rather than large copper TSVs as vertical interconnects, the IC stack 144 may support post-assembly repair. Connections throughout the IC stack 144 may be located in precise locations, and there may be enough connections to do thorough post-assembly repair. Thus, the IC stack 144 of the imager 140 may include a memory subsystem that has high density, performance, and that operates under low power.

The bypass capacitor 160 may be disposed underneath the imager 140 inside of the interior space of the needle 120. The bypass capacitor 160 may be coupled between the second stack 148 of the imager 140 and the wires 132, 134, 136, and 138, and may reduce noise in imaging data transmitted by the positive data wire 136 and the negative data wire 138. One terminal of the bypass capacitor 160 may be connected to the positive data wire 136, and a second terminal of the bypass capacitor 160 may be connected to the negative data wire 138.

The bypass capacitor 160 may be of a 0201 size, leaving a cross sectional area for injected fluids within the interior of the needle 120. Fluids may flow through the needle 120, unimpeded by the imager 140 including the first and second stacks.

In an embodiment, another bypass capacitor may be disposed underneath the imager 140, and may also reduce noise in power supplied to the imager 140 through the positive power wire 132 and the negative power wire 134. The other bypass capacitor can be coupled between the positive power wire 132 and the negative power wire 134.

Embodiments of the apparatus 100 may be manufactured at a low cost. As such, the apparatus 100 can be a single use, disposable device. The video syringe can be a cost-effective alternative to conventional arthroscopes, for example.

The control ICs among the IC stack 144 and the imaging chip 142 may be manufactured using one or more of the following manufacturing methods.

A high performance CMOS process may be used to build high performance logic circuits in the imager 140, such as sense amps, write drivers, and decoders. A dynamic random-access memory (DRAM) process can be used to build memory storage bits in the imager 140. Larger feature-size processes can be used when they offer the right capabilities at a good cost, and more expensive, advanced processes can be used when they are needed. This mix of cheaper and more expensive processes can be used to build a single, highly optimized device.

Embodiments of the imaging needle apparatus include one or more wires that connect an imager to external electronics, such as a display apparatus. As noted above, in order to reduce the effect of noise across the one or more wires, each of the wires may be coupled to the bypass capacitor 160. In an embodiment, each wire is a micro-coaxial wire, in which the bypass capacitor is incorporated into the wire itself.

Figure 7:
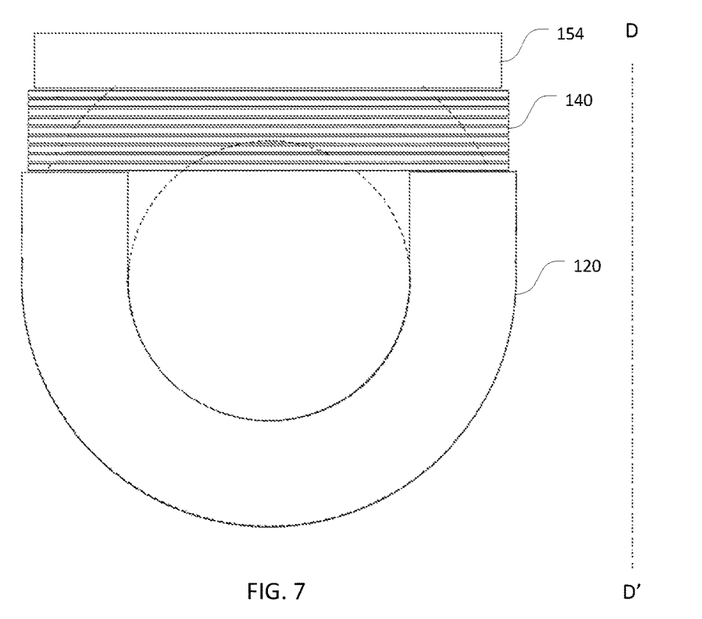
FIG. 7 illustrates a cross-section of the needle of the imaging apparatus along a line D-D' according to an embodiment of the present disclosure.

FIG. 7 illustrates a cross-section of the needle 120, imager 140, and the first LED 154 along a line D-D' illustrated in FIG. 1.

Figure 8:
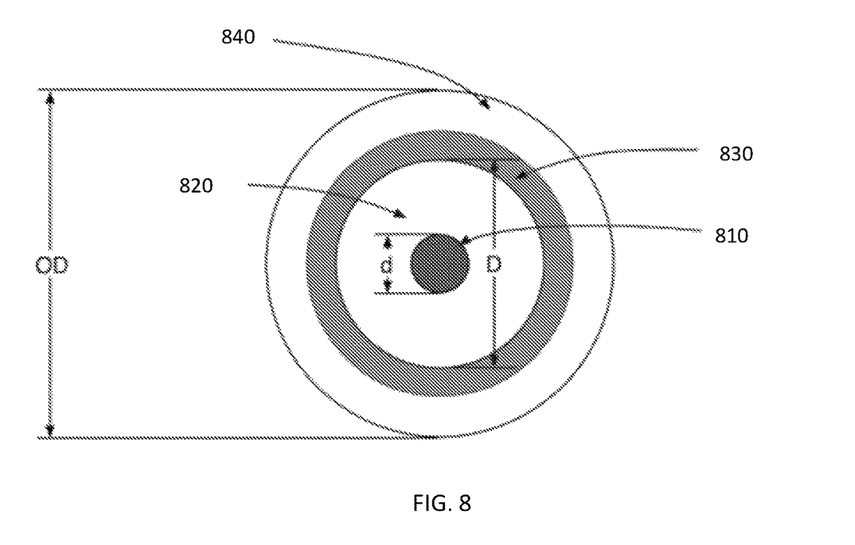
FIG. 8 illustrates a cross-section of a micro-coaxial wire according to an embodiment of the present disclosure.

FIG. 8 illustrates a cross-section of a first micro-coaxial wire according to an embodiment of the present disclosure. The first micro-coaxial wire includes an inner conductor 810 with a diameter d, an inner dielectric insulator 820 with a diameter D, an outer conductor 830, and an outer insulating jacket 840 with an outer diameter OD.

The inner conductor 810 may conduct data signals through the micro-coaxial wire. The inner conductor 810 may be a wire, and may be covered by the inner dielectric insulator 820. The inner conductor 810 may include a conductive material, such as copper. In an embodiment, the inner conductor 810 may be a positive data wire, and may be substituted for the positive data wire 136 discussed above with respect to FIGS. 1 through 5.

The inner dielectric insulator 820 may be disposed between the inner conductor 810 and the outer conductor 830. The inner dielectric insulator 820 may include a dielectric material, such as Teflon.

The outer conductor 830 may be disposed between the inner dielectric insulator 820 and the outer insulating jacket 840. The outer conductor 830 may be connected to ground. The outer conductor 830 may include copper. In an embodiment, the outer conductor 830 may be a negative data wire, and may be substituted for the negative data wire 138 discussed above with respect to FIGS. 1 through 5.

The outer insulating jacket 840 may be disposed on an outer surface of the micro-coaxial wire, and may electrically insulate the rest of the first micro-coaxial wire from the outside environment.

In an embodiment, the inner conductor 810, the inner dielectric insulator 820, and the outer conductor 830 collectively form a data bypass capacitor. When the first micro-coaxial wire is coupled to an imager, and imager data is transmitted through the inner conductor 810, the capacitor reduces the transmission of noise in imaging data transmitted from the imager to external electronics.

Figure 9:
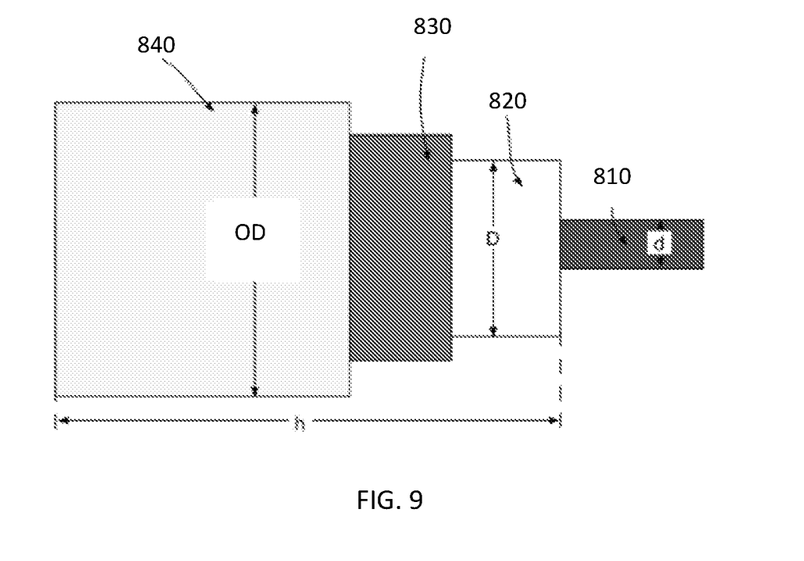
FIG. 9 illustrates a side view of the micro-coaxial wire of FIG. 8 according to an embodiment of the present disclosure.

FIG. 9 illustrates a side view of the micro-coaxial wire of FIG. 8 according to an embodiment of the present disclosure. A length of the first micro-coaxial wire h may affect its capacitance. The capacitance C of the micro-coaxial wire may be represented by Equation 1 below:

$$C = \frac{2\pi\varepsilon h}{\ln\left(\frac{D}{d}\right)} \quad \text{Equation 1}$$

Wherein ε is the capacitance of the inner dielectric insulator 820, D is the diameter of the outer conductor 830, and d is the diameter of the inner conductor 810.

The characteristic impedance Z of the micro-coaxial wire may be represented by Equation 2 below:

$$Z = \ln\left(\frac{D}{d}\right)\left(\frac{1}{2\pi}\right)\sqrt{\frac{\mu}{\varepsilon}} \quad \text{Equation 2}$$

Wherein μ is the relative permeability of the inner dielectric insulator 820.

In an embodiment, d may have a length of between 10-30 μm, D may have a length of between 50-100 μm, and Z may be equal to between 40 to 80 ohms. In a specific embodiment, d may have a length of about 25 μm, D may have a length of about 75 μm, and Z may be equal to about 50 ohms.

Figure 10:
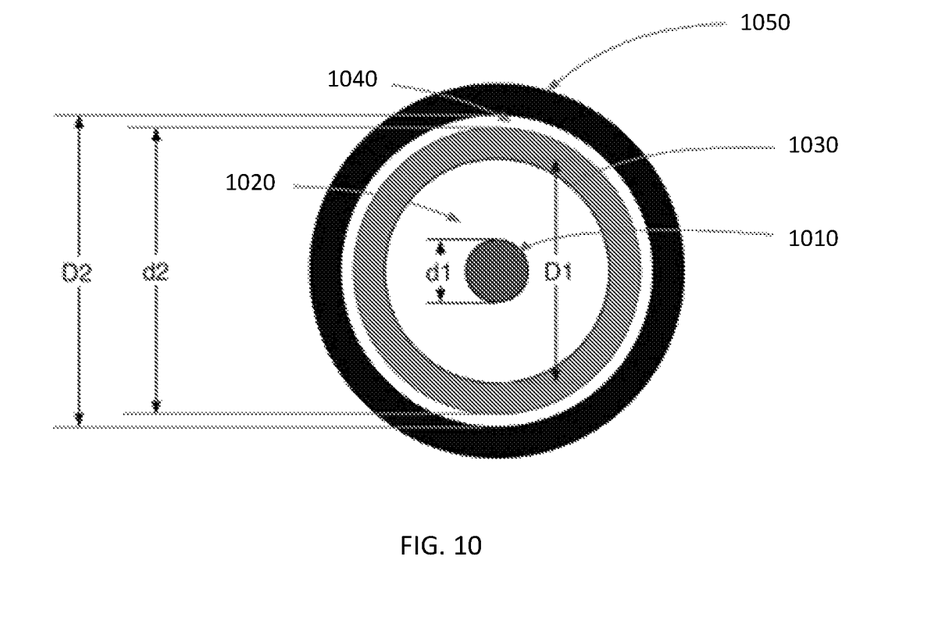
FIG. 10 illustrates a cross-section of a micro-coaxial with a power supply bypass according to an embodiment of the present disclosure.
Figure 11:
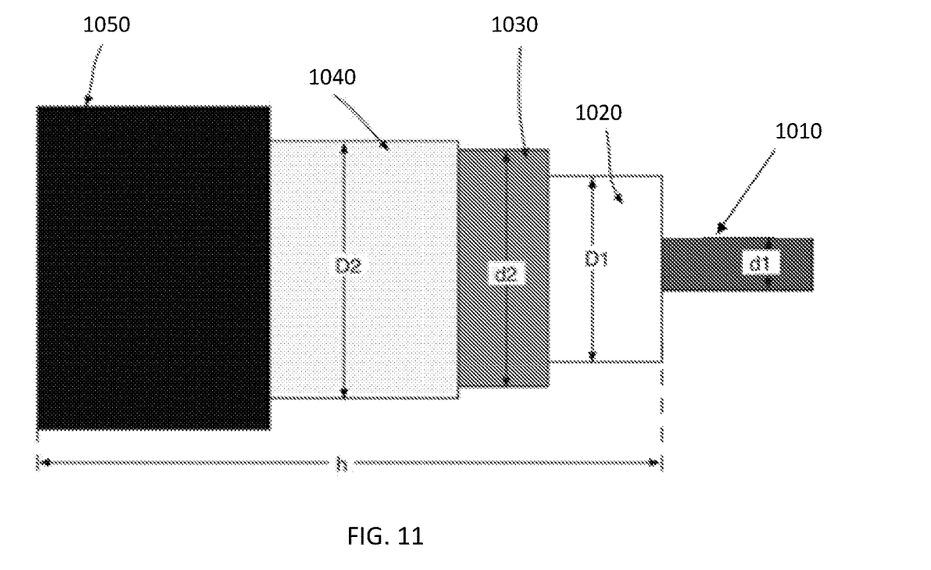
FIG. 11 illustrates a side view of the micro-coaxial with the power supply bypass of FIG. 10 according to an embodiment of the present disclosure.

FIG. 10 illustrates a cross-section of a second micro-coaxial wire according to another embodiment of the present disclosure. The second micro-coaxial wire includes a power supply bypass capacitor, as well as a data bypass capacitor, similar to the one described above with respect to FIGS. 8 and 9. FIG. 11 illustrates a side view of the second micro-coaxial with the power supply bypass of FIG. 10 according to an embodiment of the present disclosure. A length of the second micro-coaxial wire h affects the capacitance of the power supply bypass capacitor and data bypass capacitor.

The second micro-coaxial wire includes an inner conductor 1010, an inner dielectric insulator 1020, a middle conductor 1030, an outer dielectric insulator 1040, and an outer conductor 1050.

The inner conductor 1010 may transmit a data signal from an imager to outside electronics. The inner conductor 1010 may be a wire, and may include a conductive material, such as copper.

The inner dielectric insulator 1020 may be disposed between the inner conductor 1010 and the middle conductor 1030. The inner dielectric insulator 1020 may include a dielectric material, such as a polymer. The dielectric material may include Teflon.

The middle conductor 1030 may be disposed between the inner dielectric insulator 1020 and the outer dielectric insulator 1040. The middle conductor 1030 may be electrically connected to a first terminal of a power supply, such as a positive terminal of the power supply. The middle conductor 1030 may include a conductive material, such as copper.

The outer dielectric insulator 1040 may be disposed between the middle conductor 1030 and the outer conductor 1050. The outer dielectric insulator 1040 may include a dielectric material, such as a polymer. The dielectric material may include Teflon.

The outer conductor 1050 may be disposed on an outer surface of the second micro coaxial wire. The outer conductor 1050 may be electrically connected to a second terminal of the power supply, such as the negative terminal of the power supply. The outer conductor 1050 may include a conductive material, such as copper. In an embodiment, the outer conductor 1050 may be covered with an insulating material.

The second micro-coaxial wire includes two capacitors. The first capacitor includes the inner conductor 1010, the inner dielectric insulator 1020, and the middle conductor 1030. The first capacitor prevents noise from imaging data signals produced by the imager from being transmitted to external electronics along the micro-coaxial wire. That is, the first capacitor may be a data bypass capacitor. The capacitance C1 of the first capacitor may be represented by Equation 3.

$$C1 = \frac{2\pi\varepsilon_1 h}{\ln\left(\frac{D1}{d1}\right)} \qquad \text{Equation 3}$$

Wherein $\varepsilon_1$ is the dielectric constant of the inner dielectric insulator 1020, h is the length of the micro-coaxial wire, d1 is the diameter of the inner conductor 1010, and D1 is the inner diameter of the middle conductor 1030.

In an embodiment, d1 may have a length of between 10-30 μm and D1 may have a length of between 50-100 μm. In a specific embodiment, d may have a length of about 25 μm and D may have a length of about 75 μm.

The second capacitor includes the middle conductor 1030, the outer dielectric insulator 1040, and the outer conductor 1050. The second capacitor prevents noise from being transmitted from the power supply among the external electronics to the imager. The capacitance C2 of the second capacitor may be represented by Equation 4.

$$C2 = \frac{2\pi\varepsilon_2 h}{\ln\left(\frac{D2}{d2}\right)} \qquad \text{Equation 4}$$

Wherein $\varepsilon_2$ is the dielectric constant of the outer dielectric insulator 1040, h is the length of the micro-coaxial wire, d2 is the outer diameter of the middle conductor 1030, and D2 is the inner diameter of the outer conductor 1050.

The characteristic impedance Z of the micro-coaxial wire, with respect to the data signal transmitted via the inner conductor 1010, may be represented by Equation 5.

$$Z = \ln\left(\frac{D1}{d1}\right)\left(\frac{1}{2\pi}\right)\sqrt{\frac{\mu}{\varepsilon_1}} \qquad \text{Equation 5}$$

Wherein μ is the permeability of the inner dielectric insulator 1020.

In an embodiment, Z may be equal to between 40 to 80 ohms. In a specific embodiment, Z may be equal to about 50 ohms.

Figure 12:
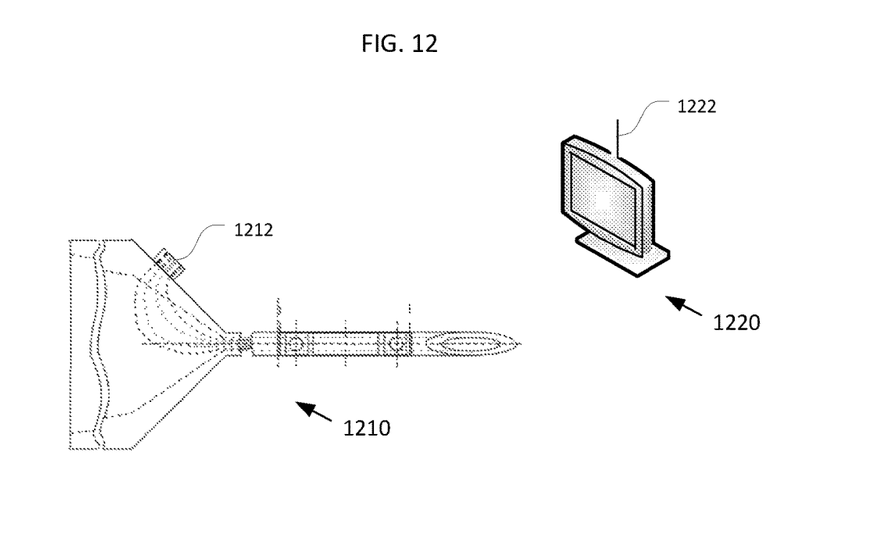
FIG. 12 illustrates a system including an imaging apparatus and a display device, according to an embodiment.

FIG. 12 illustrates a system including an imaging apparatus 1210 and a display device 1220, according to an embodiment of the present disclosure.

The imaging apparatus 1210 may be an imaging syringe that includes an imager, a needle, and a syringe. The imager may be disposed on an outer surface of the needle. A bayonet of the needle may be coupled to the syringe.

The imager may convert image signals into imaging data. The imaging data may be transferred to a wire output 1212 disposed on a side of the syringe.

In an embodiment, the wire output 1212 may be coupled to one or more wires that transfer the imaging data and power signals to and from the imager. The wire output 1212 may be coupled to a battery, and may transfer power from the battery to the imager. In an embodiment, the wire output 1212 transfers power to the imager from an external device, such as the external display device 1220 via a wired or wireless connection.

The imaging data may be converted to a standard video format by the imager of the imaging apparatus 1210, or by the wire output 1212 which may contain circuitry configured to filter and/or convert the imaging data into the standard video format. The standard video format may be an MPEG-4, Flash video, or any other suitable video format.

The wire output 1212 may transmit the imaging data to the external display device 1220. The wire output 1212 may transmit the imaging data via a cord that is coupled between the wire output 1212 and the external display device 1220.

In an embodiment, the wire output 1212 may wirelessly transmit the imaging data to the external display device 1220 via an antenna 1222 installed on the external display device 1220. The imaging data may be transmitted to the external display device 1220 via Bluetooth or Wi-Fi.

The external display device 1220 may be configured to display the imaging data gathered by the imager of the imaging apparatus 1210. The external display device 1220 may be compatible with the standard video format of the imaging data transmitted by the wire output 1212.

The external display device 1220 may display 2D images and/or videos gathered by the imager on one or more screens that can be viewed by a user. The external display device 1220 may display the transmitted imaging data in real time. The external display device 1220 may be a special- or general-purpose monitor, screen, television screen, mobile device, computer, or any other device with a screen that can display images or video to a user. In an embodiment, the external display device 1220 may be a virtual reality display.

Figure 13:
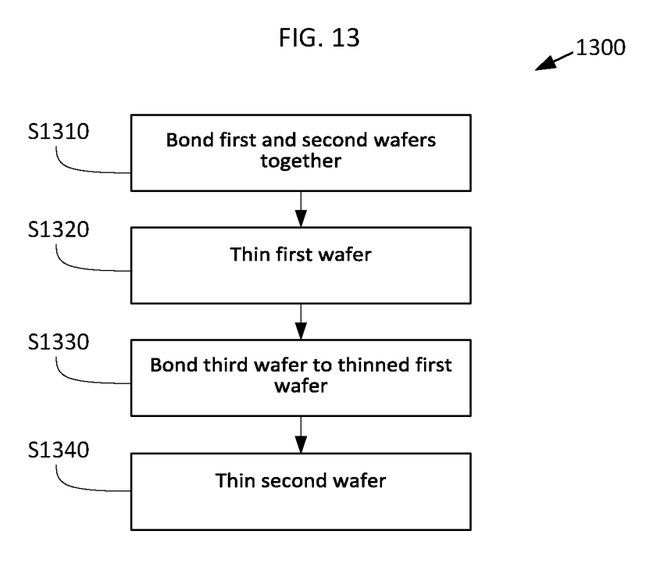
FIG. 13 is a flow-chart describing a wafer manufacturing process according to an embodiment.

Accordingly, an imaging syringe can record images or videos of a skeletal joint, and transmit the recorded images or videos to an external display device. The display device FIG. 13 is a flow-chart describing a wafer manufacturing process according to an embodiment.

Each of the stacked ICs among the stack of ICs 144 and the imaging chip 142, as described above with respect to FIGS. 4 through 7, may include a wafer manufactured using a pre-bonding process 1300.

At S1310, first and second wafers are bonded together. The first wafer is subsequently thinned at S1320. The second wafer may structurally support the first wafer while the first wafer is thinned. Accordingly, the first wafer may be thinned more aggressively than it could have been if it was not bonded to the second wafer. That is, the first wafer may be aggressively thinned without breaking the first or second wafers.

At S1330, a third wafer may be bonded to the thinned first wafer. In an embodiment, the third wafer may be attached to a plurality of additional wafers. The third wafer may provide additional structural support to the first and second wafers. Accordingly, the second wafer may be thinned at S1340.

In an embodiment, the pre-bonding process 1300 may be repeated over and over until the stack contains a plurality of layers of thinned wafers.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting.

What is claimed is:

1. An imaging device, comprising:
a needle including a tip;
an imager disposed on the needle, the imager including a plurality of stacked integrated circuits (ICs); and
a syringe coupled to the needle,
wherein the plurality of stacked ICs includes a first plurality of complementary metal-oxide semiconductor (CMOS) chips having a first size, and a second plurality of CMOS chips having a second size that is larger than the first size, the first plurality of CMOS chips being disposed between the imaging chip and the plurality of second CMOS chips.

2. The imaging device of claim 1, wherein the imager includes an imaging chip stacked on the plurality of stacked ICs, the device further comprising:
a light-emitting diode (LED) provided proximate to the imager; and
a bypass capacitor disposed inside of the needle and proximate the imager.

3. The imaging device of claim 2, wherein the imaging chip includes an array of pixels.

4. The imaging device of claim 1, wherein the imager is provided on a side of the needle.

5. The imaging device of claim 1, wherein the imager is provided proximate on a front of the needle.

6. The imaging device of claim 1, further comprising a single coaxial wire including:
an inner conductor that transmits data from the imager;
an outer conductor connected to ground;
a dielectric layer disposed between the inner conductor and the outer conductor; and
an outer insulating jacket covering the outer conductor.

7. The imaging device of claim 1, further comprising a single coaxial wire including:
an inner conductor that transmits data from the imager;
a middle conductor connected to a first power terminal;
a first dielectric layer disposed between the inner conductor and the middle conductor;
an outer conductor connected to a second power terminal; and
a dielectric layer disposed between the middle conductor and the outer conductor.

8. An imaging system, comprising:
an imaging device including a needle having a tip, an imager disposed on the needle, and a syringe coupled to the needle; and
a display electrically coupled to the imaging device,
wherein the imager includes a plurality of stacked integrated circuits (ICs) and an imaging chip stacked on the plurality of stacked ICs,
wherein the plurality of stacked ICs includes a first plurality of complementary metal-oxide semiconductor (CMOS) chips having a first size, and a second plurality of CMOS chips having a second size that is larger than the first size, the first plurality of CMOS chips being disposed between the imaging chip and the plurality of second CMOS chips.

9. The imaging system of claim 8, wherein the imaging device is electrically coupled to the display via a universal serial bus (USB) wire.

10. The imaging system of claim 8, wherein the imaging device is wirelessly coupled to the display.

11. The imaging system of claim 8, wherein the imaging chip includes an array of pixels.

12. The imaging system of claim 8, further comprising:
a wire output disposed on the syringe, and
one or more wires coupled between the imager and the wire output, the one or more wires being disposed inside of the needle.

13. The imaging system of claim 8, further comprising a single coaxial wire including:
an inner conductor that transmits data from the imager;
an outer conductor connected to ground;
a dielectric layer disposed between the inner conductor and the outer conductor; and
an outer insulating jacket covering the outer conductor.

14. The imaging system of claim 8, further comprising a single coaxial wire including:
an inner conductor that transmits data from the imager;
a middle conductor connected to a first power terminal;
a first dielectric layer disposed between the inner conductor and the middle conductor;
an outer conductor connected to a second power terminal; and
a dielectric layer disposed between the middle conductor and the outer conductor.

* * * * *